(12) United States Patent
Teichtmann

(10) Patent No.: US 8,603,133 B2
(45) Date of Patent: Dec. 10, 2013

(54) MEDICAL INSTRUMENT

(75) Inventor: Elmar Teichtmann, Villingen-Schwenningen (DE)

(73) Assignee: Karl Storz GmbH & Co. KG (DE)

( * ) Notice: Subject to any disclaimer, the term of this patent is extended or adjusted under 35 U.S.C. 154(b) by 143 days.

(21) Appl. No.: 11/947,351

(22) Filed: Nov. 29, 2007

(65) Prior Publication Data

US 2009/0018573 A1 Jan. 15, 2009

(30) Foreign Application Priority Data

Nov. 29, 2006 (DE) .......................... 10 2006 056 200

(51) Int. Cl.
*A61B 17/00* (2006.01)
(52) U.S. Cl.
USPC ........................................................ 606/205
(58) Field of Classification Search
USPC ............................ 606/106, 108, 113, 205, 208
See application file for complete search history.

(56) References Cited

U.S. PATENT DOCUMENTS

| 4,522,206 A | | 6/1985 | Whipple et al. ............... 128/312 |
| 4,662,371 A | * | 5/1987 | Whipple et al. ............... 606/170 |
| 4,986,825 A | * | 1/1991 | Bays et al. ....................... 604/22 |
| 5,700,276 A | * | 12/1997 | Benecke ......................... 606/208 |
| 5,814,055 A | * | 9/1998 | Knodel et al. .................. 606/151 |
| 5,868,786 A | * | 2/1999 | DiFrancesco .................. 606/208 |
| 5,951,587 A | * | 9/1999 | Qureshi et al. ................. 606/207 |
| 6,579,304 B1 | * | 6/2003 | Hart et al. ...................... 606/207 |

FOREIGN PATENT DOCUMENTS

| DE | 3716764 A1 | 12/1988 |
| DE | 4444403 A1 | 6/1996 |
| DE | 195 21 257 | 12/1996 |
| DE | 196 32 298 | 2/1998 |
| DE | 696 24 770 | 7/2003 |

OTHER PUBLICATIONS

European Search Report; EP 07 02 2912; Jun. 3, 2009; 7 pages.
German Search Report, dated Jun. 11, 2007, 4 pages.

* cited by examiner

*Primary Examiner* — Katherine Dowe
*Assistant Examiner* — Amy Shipley
(74) *Attorney, Agent, or Firm* — St. Onge Steward Johnston & Reens LLC

(57) ABSTRACT

The invention relates to a medical instrument having a hollow shaft, a tool positioned on the distal end of the shaft consisting of a rigid jaw member and a jaw member that can rotate with respect to the rigid jaw member, as well as a handle positioned on the proximal end of the shaft. The tool and the handle are in active connection with one another by a push-pull rod mounted in the shaft, and the jaw members of the tool are mounted on one another by pins. It is proposed with the invention that the push-pull rod should be configured as a hollow slide tube mounted in the shaft so that it can slide axially and is in active connection with the rotatable jaw member by an actuation element that is essentially rod-shaped.

10 Claims, 4 Drawing Sheets

Fig. 4
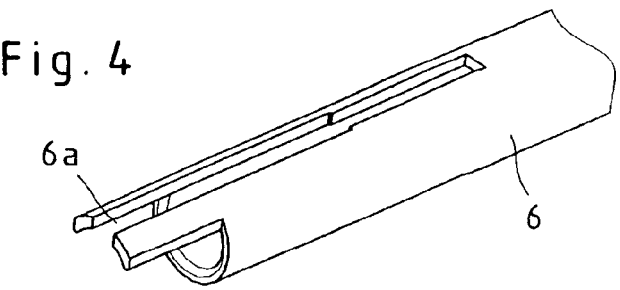
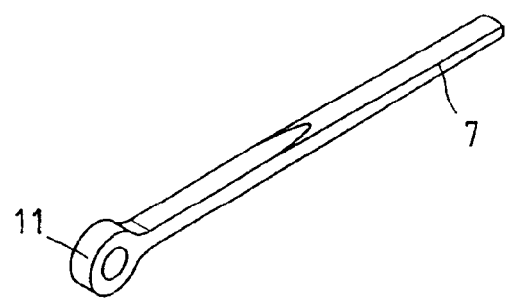
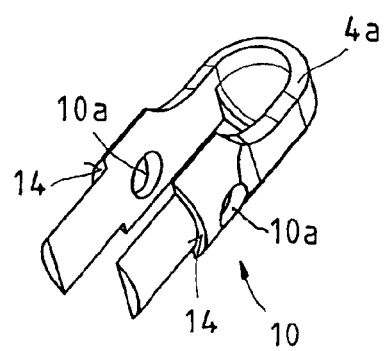
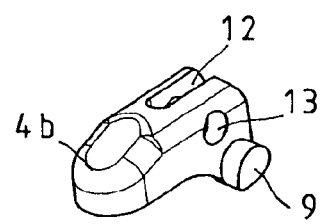
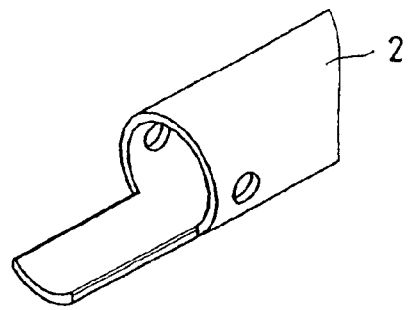

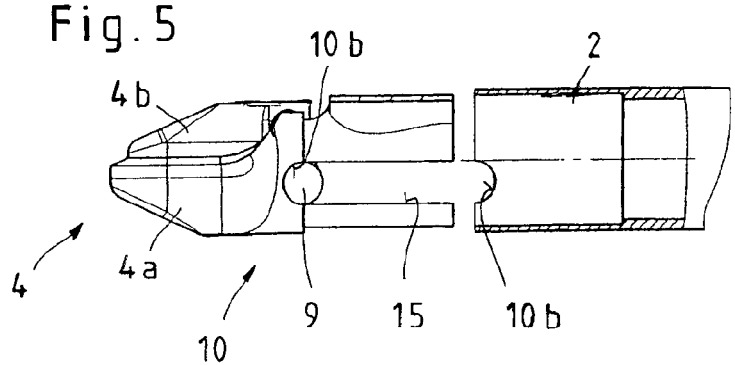
Fig. 5
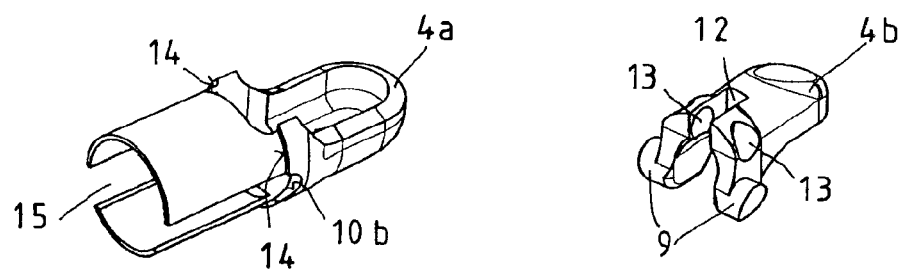
Fig. 6
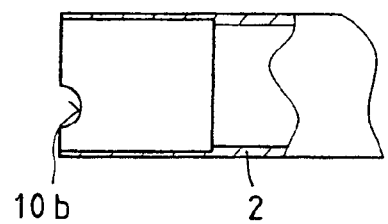

MEDICAL INSTRUMENT

CROSS-REFERENCE TO RELATED APPLICATIONS

The present application claims priority of German patent application No. 10 2006 056 200.3 filed on Nov. 29, 2006, the content of which is incorporated herein by reference.

FIELD OF THE INVENTION

The invention relates to a medical instrument having a hollow shaft, a tool positioned on the distal end of the shaft and consisting of a rigid jaw member and a jaw member that can rotate with respect to the rigid jaw member, as well as a handle mounted on the proximal end of the shaft, wherein the tool and the handle are in active connection with one another by way of a push-pull rod mounted in the shaft and wherein the jaw members of the tool are rotatably mounted on one another by correspondingly shaped mounting pins.

BACKGROUND OF THE INVENTION

Generic medical instruments are frequently employed in the art as cutting, stamping, gripping, and/or holding tools. Common to these medical instruments is that the rotatable jaw member of the tool can be actuated by the push-pull rod with as little free play as possible and with sufficient force transmission. A generic medical instrument is reported in the art, for instance, in DE 195 21 257 A1. With this known instrument, the two jaw members are mounted onto one another by The invention relates to a medical instrument having a hollow shaft, a tool positioned on the distal end of the shaft and consisting of a rigid jaw member and a jaw member that can rotate with respect to the rigid jaw member, as well as a handle positioned on the proximal end of the shaft, where the tool and the handle are in active connection with one another by means of a push-pull rod mounted in the shaft, and where the jaw members of the tool are mounted on one another by molded mounting pins Generic medical instruments are frequently used in the art as cutting, stamping, gripping, and/or holding tools. Common to these medical instruments is the fact that the rotatable jaw member of the tool is actuated by the push-pull rod in a manner allowing the least possible free play and with sufficient force transmission.

A generic medical instrument is described, for instance, in DE 195 21 257 A1. In this known instrument the two jaw members are mounted on one another by means of mounting bolts molded to the movable jaw member. The push-pull rod for actuating the jaw members is extended in the longitudinal direction through the hollow instrument shaft and on both sides leaves a longitudinally extending lumen free which can be used as a rinsing channel. Because in endoscopic instruments the outer diameters of the instrument shafts measure only 2 mm or less, this lumen that remains free between the push-pull rod and the shaft interior forms a rinsing channel with a very small channel cross-section.

An additional medical instrument is known, for instance, from U.S. Pat. No. 4,522,206. In this known medical instrument, the rotatable jaw member is mounted on the rigid jaw member by two axle spindles that can be inserted into corresponding mounting bore-holes in the two jaw members. This construction is disadvantageous in various respects, first because the use of the individual axle spindles that are to be inserted into the mounting bore-holes in installation is complex and time-consuming and second because instruments with very small outer diameter cannot be produced in this configuration.

SUMMARY OF THE INVENTION

Consequently it is the object of the invention to produce a medical instrument of the aforementioned type which while having a small outer diameter is of simple construction and easy to install.

The fulfillment of this object according to the invention is characterized in that the push-pull rod is configured as a hollow slide tube that is mounted so that it can slide axially in the shaft and that is in active connection with the rotatable jaw member by means of an essentially rod-shaped actuation element.

This embodiment with the hollow slide tube is particularly advantageous when the hollow instrument shaft is intended to be enabled for use as a suction and/or rinsing channel.

To ensure especially good force transmission from the push-pull rod to the rotatable jaw member, the rod-shaped actuation element is mounted so that one end can pivot on the rotatable jaw member and so that the other end is connected with the slide tube. The actuation element is advantageously of spring-elastic configuration or spring-elastically mounted in order to be able, with the purely axial pushing of the slide tube, to follow the arch-shaped path of the pivot point of the actuation element on the rotatable jaw member, wherein the rod-shaped actuation element and the rotatable jaw member according to the invention are mounted on a common mounting pin.

Owing to the direct molding of the mounting pins on the jaw members of the tool, the number of the components to be connected with one another during installation is reduced and the installation is thereby simplified. In addition, the inventive configuration also makes possible the production of instruments having a small outer diameter of 2 mm for instance and less, because the molded mounting pins do not still need to be riveted or soldered.

According to a preferred embodiment of the invention it is proposed that two mounting pins are positioned on one jaw member and that they can be inserted into corresponding mounting recesses of the other jaw member. Owing to the configuration of the two mounting pins on just one of the two jaw members, the installation is simplified.

According to a practical embodiment of the invention it is proposed that the mounting pins should be positioned on the rotatable jaw member and the mounting recesses should take the form of bore-holes in the rigid jaw member.

With a second practical embodiment of the invention it is proposed that the mounting pins should be positioned on the rotatable jaw member and the mounting recesses should be configured as mounting segments shaped in the rigid jaw member and in the shaft. This embodiment of the mounting recesses as positioned halfway in the rigid jaw member and halfway in the shaft tube constitutes an especially simple and rapid structure in terms of installation.

It is finally proposed with the invention that the rotatable jaw member and the push-pull rod should be configured as a component that can be pre-assembled. In addition to the reduction of the number of components owing to the inventive direct molding of the mounting pins on the jaw members, the installation can be further simplified in that individual components such as the rotatable jaw member and the push-pull rod can be pre-assembled as component groups which then are to be connected with the remaining units only as needed.

Additional characteristics and advantages of the invention can be seen from the related illustrations, in which two embodiments of an inventive medical instrument are shown in merely exemplary fashion, without restricting the invention to this embodiment.

BRIEF DESCRIPTION OF THE DRAWINGS

FIG. 4 shows a perspective general view of the individual components of the distal end according to FIGS. 2 and 3.

FIG. 5 shows a side view of detail V depicting the distal end of the medical instrument according to FIG. 1 and showing a second inventive embodiment.

FIG. 6 shows a perspective general view of the individual components of the distal end according to FIG. 5.

DETAILED DESCRIPTION OF THE INVENTION

Figure 1:
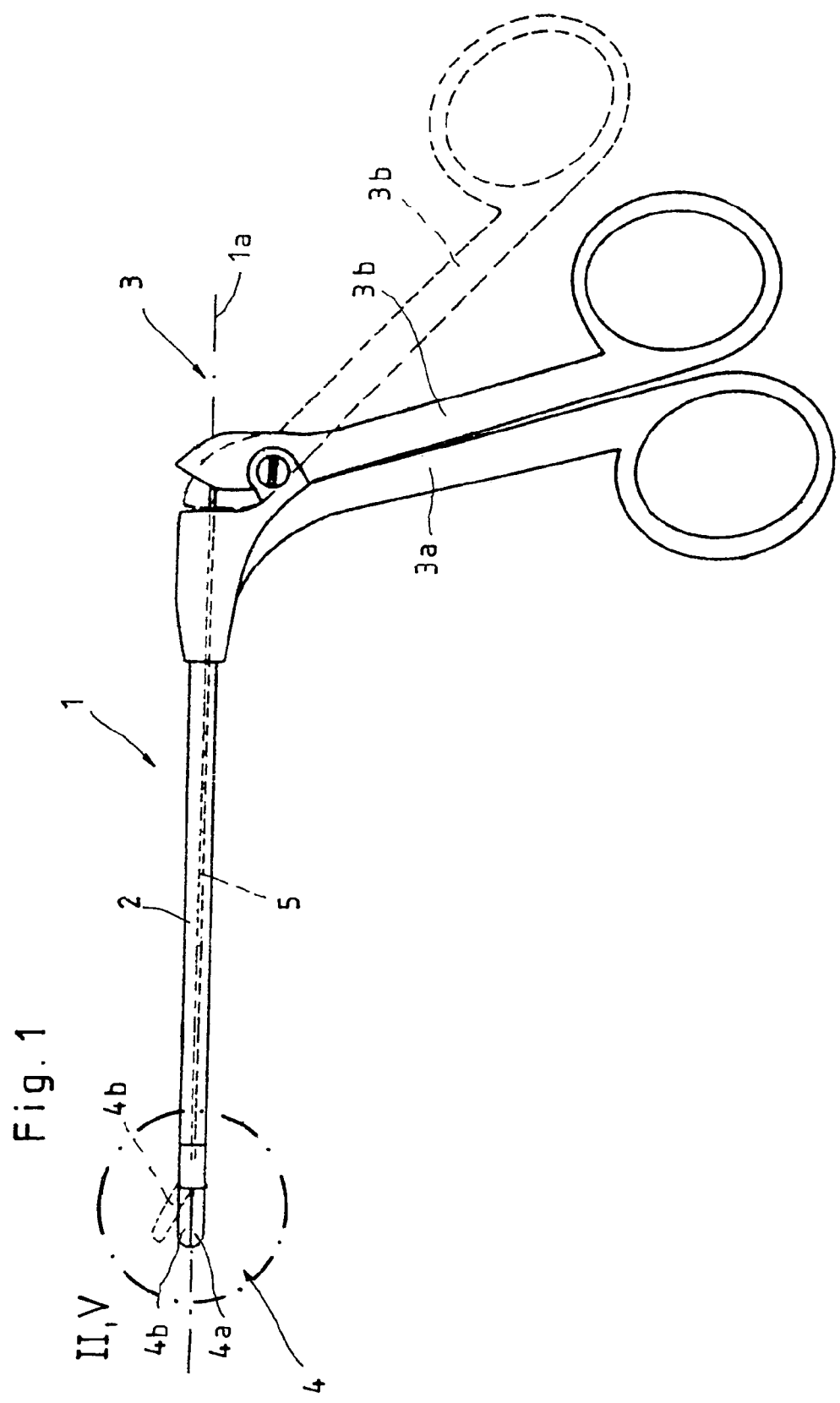
FIG. 1 shows a schematic side view of an inventive medical instrument.

The first illustration (FIG. 1) shows the side view of a medical instrument whose power transmission mechanism has multiple uses such as for punches, scissors, needle holders, gripping instruments, and the like.

The simplified graphic view of the medical instrument 1 consists essentially of a hollow shaft 2 on whose proximal end a handle 3 is configured which consists of a rigid gripping member 3a and a gripping member 3b that can rotate with respect to the rigid gripping member 3a. On the distal end of the shaft, a tool 4 is positioned which consists of a rigid jaw member 4a and a jaw member 4b that con rotate with respect to the rigid jaw member 4a.

As can be seen from FIG. 1, the rotatable jaw member 4b of the tool 4 and the rotatable gripping member 3b of the handle 3 are—by means of a push-pull rod 5 that is mounted in the hollow shaft 2 so that it can slide axially—in active connection with one another in such a way that the jaw member 4b of the tool 4 can be transferred from the closed position (shown with solid lines in FIGS. 1 and 5) into the open position (shown with dots in FIGS. 1, 2, and 3) or vice versa by means of the displacement of the gripping member 3b of the handle 3.

Figure 3:
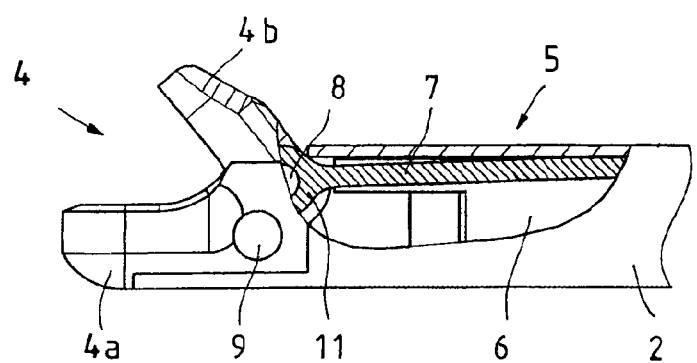
FIG. 3 shows a partly cut-out side view of the version of FIG. 2.

As can be seen from FIG. 3, the push-pull rod 5 in the illustrated medical instrument 1 consists of a hollow slide tube 5 that is mounted so that it slides axially in the hollow shaft 2 and an essentially rod-shaped actuation element 7, which, affixable in a slit 6a of the slide tube 6, forms the actual connection between the push-pull rod 5 and the rotatable jaw member 4b. For this purpose the rod-shaped actuation element 7 is mounted so that one end is mounted on the rotatable jaw member 4b of the tool 4 so that it can rotate by means of a mounting pin 8 and the other end is connected on the other end with the slide tube 6. The configuration of the push-pull rod 5 with a hollow slide tube 6 serves especially for medical instruments 1 such as suction punches whose hollow shaft serves as a suction and/or rinsing channel.

The structure of the jaw members 4a and 4b of the tool 4 results in particular from FIG. 4 (for the first embodiment) and FIG. 6 (for the second embodiment). As can be seen from FIGS. 4 and 6 together with the related illustrations FIGS. 3 and 5, the jaw members 4a, 4b in the illustrated embodiments are configured in such a way that protruding mounting pins 9 extending laterally outward are shaped on the rotatable jaw members 4b, by which mounting pins 9 the rotatable jaw members 4b can be mounted on the rigid jaw members 4a. As intake for the mounting pins 9 of the respective rotatable jaw member 4b, the related rigid jaw member 4a comprises intake parts 10 that correspond to the mounting pins 9.

Alternatively to the illustrated embodiments with mounting pins 9 molded exclusively to the rotatable jaw member 4b, it is also possible of course to configure the mounting pins 9 exclusively on the rigid jaw member 4a or else with one mounting pin 9 each on the rigid jaw member 4a and one mounting pin on the rotatable jaw member 4b, so that then each other jaw member 4a or 4b the corresponding mounting recesses 10 are configured for mounting intake of the mounting pins 9.

Configuring the mounting sites of the jaw member 4a and 4b as mounting pins 9 molded directly on the jaw member 4b has the advantage that the mounting site can be shoved all the way to the border of the component and requires no wall or material strength in order to configure bore-holes known in the art for intake of a mounting pin. This displacement of the mounting site outward onto the border of the component offers advantages for the lever length and thus for the power transmission, because such a great distance can be achieved between the mounting site of the rotatable jaw member 4b and the gripping point of the actuation element 7 of the push-pin rod 5 on the rotatable jaw member 4b.

The two embodiments illustrated in FIGS. 2 through 4 and FIGS. 5 and 6 are distinguished from one another by the configuration of the mounting intake parts 10 that serve as intake for the mounting pins 9 of the rotatable jaw member 4b.

Figure 2:
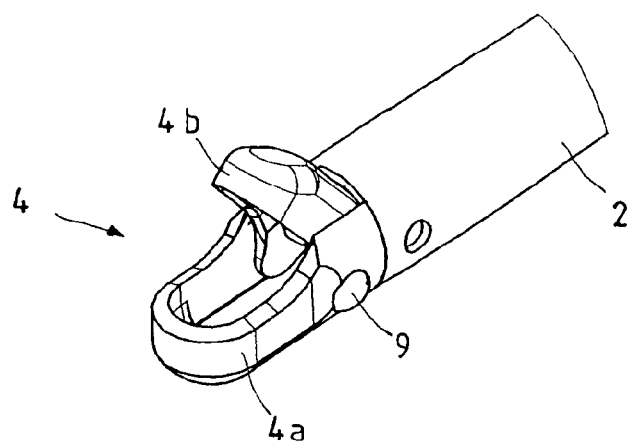
FIG. 2 shows a perspective view of detail 11 depicting the distal end of the medical instrument according to FIG. 1, showing a first inventive embodiment.

In the first embodiment according to FIGS. 2 through 4, the mounting intake part 10 is configured as a mounting borehole 10 in the rigid jaw member 4a, so that in the side walls of the rigid jaw member 4a in each case one mounting bore-hole 10a is configured which, with the tool 4 fully installed, fully surround the mounting pins 9 of the rotatable jaw member 4b.

On the other hand the mounting recesses 10 in the second embodiment illustrated in FIGS. 5 and 6 consist of mounting segments 10b that are configured in the rigid jaw member 4a as well as in the shaft 2 and which, only when the tool 4 and shaft 2 are completely installed, form the mounting recesses 10 that completely surround the mounting pins 9.

The construction of the distal areas of the medical instrument 1 illustrated in FIGS. 2 through 6 occurs as follows:

In a first working step, the actuation element 7 is inserted into the slit 6a of the slide tube 6 to complete the push-pull rod 5 and is soldered with the rotatable jaw member 4b. To connect the actuation element 7 with the rotatable jaw member 4b, in the distal end of the actuation element 7 a grommet 11 is configured in the distal end of the actuation element 7 for intake of the mounting pin 8, and said grommet can be inserted into a notch 12 configured in the proximal end of the rotatable jaw member 4b in such a way that the grommet 11 is flush with two mounting bore-holes 13 configured in the rotatable jaw member 4b. In this position, the actuation element 7 is now connected permanently with the rotatable jaw member 4b by means of the mounting pin 8, so that the push-pull rod 5 along with the rotatable jaw member 4b are configured as a prefabricated unit.

Because the mounting pin 8 and the actuation element 7 mounted on the mounting pin 8 moves in a circular arc around the mounting site of the rotatable jaw member 4b on the rigid jaw member 4a when the jaw member 4b is rotated, it is advantageous to solder the actuation element 7 as far as possible proximally in the slit 6a with the slide tube 6 in order to configure the actuation element 7 as spring-elastic.

To prevent overtaxing of the mounting pin 8, inside the shaft or the slide tube 6 it is possible to configure abutment surfaces with which the rotatable jaw member 4b comes in contact in the closed position. These abutment surfaces prevent too deep an insertion of the rotatable jaw member 4b into the rigid jaw member 4a upon closing of the tool 4.

This aforementioned working step with the configuration of the prefabricated components as push-pull rod 5 and a rotatable jaw member 4b is identical in both illustrated embodiments.

To complete the tool 4, thereafter the rotatable jaw member 4b and the rigid jaw member 4a must be connected with one another. Because of the different configurations of the mounting recesses 10 in the two illustrated embodiments of a medical instrument 1, the following working steps for installing the two medical instruments 1 differ from one another.

In the first embodiment depicted in FIGS. 2 through 4, the fork-shaped proximal end of the rigid jaw member 4a is first spread apart by outward bending of the side walls and then the rotatable jaw member 4b is inserted into the spread-apart proximal end of the rigid jaw member 4a until the molded mounting pins 9 are flush with the mounting bore-holes 10a. As soon as the mounting pins 9 enter into the mounting bore-holes 10a, the spread-apart proximal end of the rigid jaw member 4a jumps back into its starting position and affixes the two jaw members 4a and 4b to one another.

Alternatively it is also possible, however, to press together the proximal end of the rotatable jaw member 4b that is likewise configured in fork-shape by the notch 12 and subsequently to insert it into the fork-shaped proximal end of the rigid jaw member 4a until the molded mounting pins 9 are flush with the mounting bore-holes 10a. As soon as the mounting pins 9 are flush with the mounting bore-holes 10a, the pressed-together proximal end of the rotatable jaw member 4b jumps back into its starting position and affixes the two jaw members 4a and 4b to one another.

Next the hollow shat 2 is pushed by the slide tube 6 from the proximal end until the distal end of the shaft 2 is contiguous with abutment surfaces 14 of the rigid jaw member 4a and is connected permanently, for instance by soldering, with the rigid jaw member 4a.

In the second embodiment illustrated in FIGS. 5 and 6, two oppositely placed elongated holes 15 for insertion of the mounting pins of the rotatable jaw member 4b are configured in the proximal end of the rigid jaw member 4a. The mounting segments 10b form the distal ends of the elongated holes 15. In a first step for completing the tool 4, the molded mounting pins 9 of the rotatable jaw member 4b are inserted into the elongated holes 15 and the rotatable jaw member 4b is pushed in the distal direction until the mounting pins 9 have reached the mounting segments 10b and thus the distal end of the elongated holes 15.

Then the hollow shaft 1 is pushed from the end by the slide tube 6 until the distal end of the shaft 2 is contiguous with the abutment surfaces 14 of the rigid jaw member 4a. To complete the mounting insertion 10 in the distal end of the shaft 2, semicircular recesses are configured as mounting segments 10b which, in the position pushed upward onto the rigid jaw member 4a and with the mounting segments 10b of the rigid jaw member 4a, form mounting recesses 10 that completely surround the mounting pins 9.

Medical instruments 1 of the previously described configuration are characterized in that they are of simple construction and easily installed and in addition make possible the production of medical instruments with reduced outer diameter.

What is claimed is:

1. A medical instrument comprising:
   a hollow shaft;
   a tool positioned on a distal end of said shaft, said tool having a rigid jaw member and a rotatable jaw member that rotates with respect to said rigid jaw member, said rigid jaw member and said rotatable jaw member being mounted on one another by mounting pins;
   a handle positioned on a proximal end of said shaft;
   a push-pull rod mounted in said shaft, said push-pull rod providing active connection between said tool and said handle, said push-pull rod comprising a hollow slide tube that is adapted to slide axially in said shaft and connect with said rotatable jaw member by means of an actuation element, said actuation element being essentially rod-shaped; and
   said rigid jaw member of said tool being a separate unit which is connectable to said distal end of said shaft via said mounting pins which are formed on an outside of and in one piece with said rotatable jaw member;
   wherein said distal end of said shaft has substantially semi-circular-shaped distally-facing recesses and a proximal end of said rigid jaw member has substantially semicircular-shaped proximally-facing recesses such that, in connecting said rigid jaw member with said shaft, said distally-facing recesses and said proximally-facing recesses form mounting recesses which completely surround said mounting pins.

2. The medical instrument according to claim 1, characterized in that the actuation element is mounted on the rotatable jaw member with one end and on the slide tube with the other end.

3. The medical instrument according to claim 2, characterized in that the actuation element and the rotatable jaw member are mounted on a common mounting rod.

4. The medical instrument according to claim 2, characterized in that the actuation element has a spring-elastic configuration.

5. The medical instrument according to claim 1, characterized in that the actuation element has a spring-elastic configuration.

6. The medical instrument according to claim 5, characterized in that the actuation element and the rotatable jaw member are mounted on a common mounting rod.

7. The medical instrument according to claim 1, characterized in that the rigid jaw member and the rotatable jaw member of the tool are connected to one other before connecting the rigid jaw member with the shaft.

8. The medical instrument according to claim 1, characterized in that two mounting pins are positioned on the rotatable jaw member and are insertable into the mounting recesses.

9. The medical instrument according to claim 8, characterized in that the mounting recesses are configured as mounting bore-holes in the rigid jaw member.

10. The medical instrument according to claim 1, characterized in that the rotatable jaw member and the push-pull rod are configured as components that are pre-installed.

* * * * *